United States Patent [19]

Sircar et al.

[11] Patent Number: 4,521,416
[45] Date of Patent: Jun. 4, 1985

[54] 4,5-DIHYDRO-6-[(SUBSTITUTED)-1H-IMIDAZOL-4-YL OR 5-YL]-3(2H)-PYRIDAZINONES AND 6-[(SUBSTITUTED)-1H-IMIDAZOL-4-YL OR 5-YL]-3(2H)-PYRIDAZINONES

[75] Inventors: Ila Sircar; James A. Bristol, both of Ann Arbor, Mich.

[73] Assignee: Warner-Lambert Company, Morris Plains, N.J.

[21] Appl. No.: 477,697

[22] Filed: Mar. 22, 1983

[51] Int. Cl.$^3$ .................. A61K 31/50; C07D 237/06
[52] U.S. Cl. .................................... 514/252; 544/238; 544/239
[58] Field of Search ............... 544/238, 239; 424/250

[56] References Cited

U.S. PATENT DOCUMENTS 4,353,905 10/1982 Sircar .................................. 424/250
4,361,563 11/1982 Austel et al. ...................... 544/238
4,399,137 8/1983 Steiner et al. ..................... 424/250

Primary Examiner—Nicholas S. Rizzo
Attorney, Agent, or Firm—Jerry F. Janssen

[57] ABSTRACT 4,5-Dihydro-6-[(substituted)-1H-imidazol-4-yl or 5-yl]-3(2H)-pyridazinones 6-[(substituted)-1H-imidazol-4-yl or 5-yl]-3(2H)-pyridazinones and pharmaceutically acceptable acid addition salts thereof are useful as cardiotonic and antihypertensive agents.

The above compounds cause a significant increase in myocardial contractility in the dog and also cause a decrease in blood pressure in the spontaneously hypertensive rat. The compounds are produced by reacting the appropriate γ-oxo-imidazolebutanoic acid with a suitably substituted hydrazine to provide 4,5-dihydro-6-(substituted)imidazolyl-3(2H)-pyridazinones which are oxidized to 6-(substituted)imidazolyl-3(2H)-pyridazinones.

10 Claims, No Drawings

4,5-DIHYDRO-6-[(SUBSTITUTED)-1H-IMIDAZOL-4-YL OR 5-YL]-3(2H)-PYRIDAZINONES AND 6-[(SUBSTITUTED)-1H-IMIDAZOL-4-YL OR 5-YL]-3(2H)-PYRIDAZINONES

BACKGROUND OF THE INVENTION

U.S. Pat. No. 4,353,905 describes 4,5-dihydro-6-[4-(1H-imidazol-1-yl)-phenyl]-3(2H)-pyridazinones and 6-[4-(1H-imidazol-1-yl)phenyl]-3(2H)-pyridazinones as cardiotonic agents.

The present invention relates to 4,5-dihydro-6-[(substituted)-1H-imidazol-4-yl)]-3(2H)-pyridazinones and 6-[(substituted)-1H-imidazol-5-yl)]-3(2H)-pyridazinones as cardiotonic and antihypertensive agents.

SUMMARY AND DETAILED DESCRIPTION

The present invention relates to novel 4,5-dihydro-6-[(substituted)-1H-imidazol-4-yl or 5-yl]-3(2H)-pyridazinones and 6-[(substituted)-1H-imidazol-4-yl or 5-yl]-3(2H)-pyridazinones having the formula:

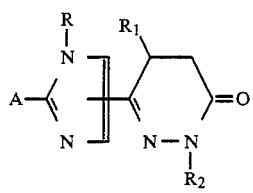

I wherein ===== represents a single or double bond; A is hydrogen, lower alkyl, phenyl, phenyl substituted by lower alkyl, halo or trifluoromethyl, or pyridinyl; R,R$_1$, and R$_2$ are independently hydrogen or lower alkyl and pharmaceutically acceptable acid addition salts thereof.

The compounds of formula I where R is lower alkyl are prepared as described below as mixtures of two positional isomers which can be separated by crystallization techniques. The two isomers are the 4,5-dihydro-6-[1-(lower alkyl)-1H-imidazol-4-yl]-3(2H)-pyridazinones and the 4,5-dihydro-6-[1-(lower alkyl)-1H-imidazol-5-yl]-3(2H)-pyridazinones.

The compounds of formula I where R$_2$ is hydrogen and ===== signifies a double bond may exist in tautomeric forms, that is, as 6-[(substituted)-1H-imidazol-4-yl or 5-yl]-3(2H)-pyridazinones of formula II or as 6-[(substituted)-1H-imidazol-4-yl or 5-yl]-3-pyridazinols of formula IIA as follows:

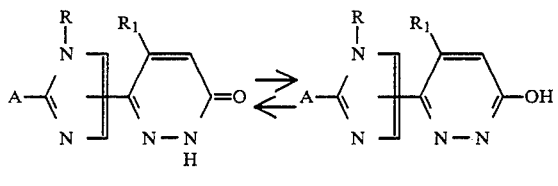

The present invention relates to compounds of the formulae III and IV

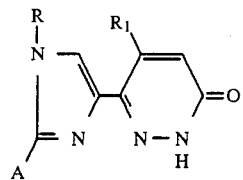

III

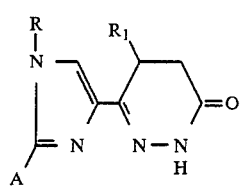

IV wherein R and R$_1$ are independently hydrogen or methyl and A is phenyl, and pharmaceutically acceptable salts thereof.

A specific aspect of the present invention is 4,5-dihydro-6-(1-methyl-2-phenyl-1H-imidazol-4-yl)-3(2H)-pyridazinone and 6-(1-methyl-2-phenyl-1H-imidazol-4-yl)-3(2H)-pyridazinone, and pharmaceutically acceptable salts thereof.

The present invention further relates to a pharmaceutical composition for increasing cardiac contractility and/or for lowering blood pressure comprising an effective amount of a compound of formula I and a pharmaceutically acceptable carrier.

Another aspect of the present invention relates to a method for increasing cardiac contractility in a patient requiring such treatment which comprises administering orally or parenterally to such patient an effective amount of a compound of formula I and a pharmaceutically acceptable carrier.

Still another aspect of the present invention relates to a method of lowering blood pressure in a patient suffering from hypertension which comprises administering orally or parenterally to such patient an effective amount of a compound of formula I and a pharmaceutically acceptable carrier.

The compounds of formula I are prepared by a process which comprises reacting a γ-oxobutanoic acid of the formula

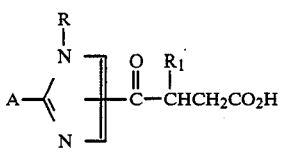

wherein A, R, and R$_1$ are as defined in the compounds of formula I, with a R$_2$-hydrazine, in which R$_2$ is also as defined in the componds of formula I, in an acid/alcohol mixture, such as ethanol/acetic acid, at elevated temperatures, such as from 50°–100° C., and preferably at about 85° C., to produce a compound of the formula

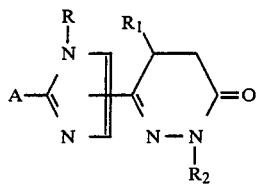

which, when desired, is converted to a compound of the formula

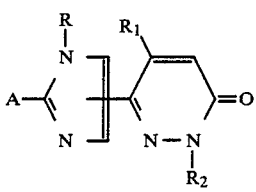

with an oxidizing agent such as manganese dioxide or m-nitrobenzenesulfonic acid according to a procedure described by W. V. Curran and A. Ross in *J. Med. Chem.*, 17, 273 (1974).

The compounds of the formula I where Q is sulfur may be conveniently prepared from the corresponding compounds of the formula I where Q is oxygen by treatment with phosphorus pentasulfide.

The compounds of formula I are useful both in the free base form and in the form of acid addition salts. Both forms are within the scope of the invention. The acid addition salts are a more convenient form for use; and in practice, use of the salt form amounts to use of the base form. In practicing the invention, it was found convenient to form the sulfate, phosphate, or methanesulfonate salts. However, other appropriate pharmaceutically acceptable salts within the scope of the invention are those derived from mineral acids such as hydrochloric acid and sulfamic acid; and organic acids such as ethanesulfonic acid, benzenesulfonic acid, p-toluenesulfonic acid, and the like, giving the hydrochloride, sulfamate, ethane-sulfonate, benzenesulfonate, p-toluenesulfonate, and the like, respectively.

The acid addition salts of said basic compounds are prepared either by dissolving the free base in aqueous or aqueous alcohol solution or other suitable solvents containing the appropriate acid and isolating the salt by evaporating the solution, or by reacting the free base and acid in an organic solvent, in which case the salt separates directly or can be obtained by concentration of the solution.

The term "lower alkyl" used above refers to a straight or branched hydrocarbon chain having from one to six carbon atoms. For example, the term includes methyl, ethyl, n-propyl, isopropyl, n-butyl, sec-butyl, tert-butyl, amyl, and the like. The term "halo" used above refers to the halogen series such as fluoro, chloro, bromo, and iodo.

The starting γ-oxobutanoic acids are prepared by methods known in the art and as illustrated by the following reaction scheme:

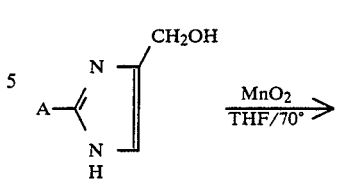

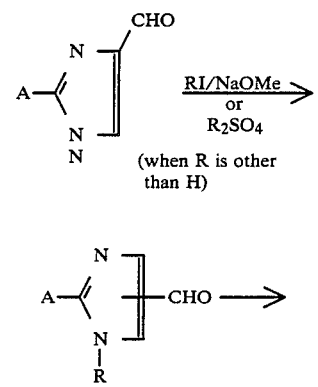

mixture of 2 isomers

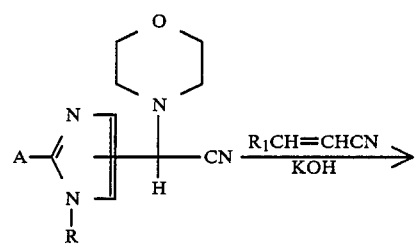

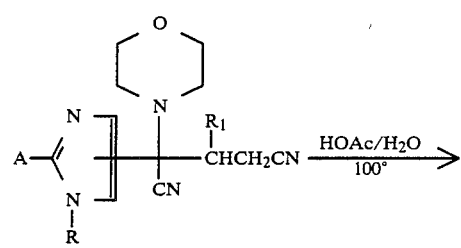

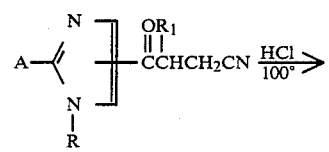

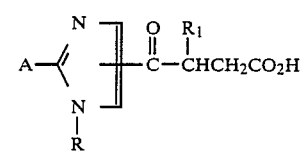

The following Examples will further illustrate the invention without, however, limiting it thereto.

EXAMPLE 1

4,5-Dihydro-6-(1-methyl-2-phenyl-1H-imidazol-4yl)-3(2H)-pyridazinone (Isomer A) and 4,5-Dihydro-6-(1-methyl-2-phenyl-1H-imidazol-5-yl)-3(2H)-pyridazinone (Isomer B)

2-Phenylimidazolyl-4-carboxaldehyde

A rapidly stirred mixture of 35.0 g (0.2 mole) of 2-phenyl-4-hydroxymethylimidazole, P. Dziuron and W. Schunack, Arch. Pharm., 306, 349 (1973), and 102.0 g (1.2 mole) of manganese dioxide (Aldrich Chemical Co.) in 1500 ml of dry tetrahydrofuran is stirred overnight at 23° C. and then refluxed for six hours. After cooling to room temperature, the catalyst is filtered off and washed with 500 ml of tetrahydrofuran. The combined filtrate and washing are evaporated in vacuo and the residue is recrystallized from acetonitrile-tetrahydrofuran giving 23.0 g of analytically pure 2-phenylimidazolyl-4-carboxaldehyde, mp 169°–170° C. Concentration of the filtrate to a low volume and cooling gives 4.0 g (total yield: 76%) of additional product, mp 169°–170° C.

Anal. calcd for $C_{10}H_8N_2O$: C, 65.75; H, 4.68; N, 16.27. Found: C, 65.52; H, 4.83; N, 16.06.

1-Methyl-2-phenylimidazolyl-4-carboxaldehyde (A) and 1-Methyl-2-phenylimidazolyl-5-carboxaldehyde (B)

Method A

To a stirred solution of 15.3 g (0.089 mole) of 1-methyl-2-phenyl-1H-imidazole-4-carboxaldehyde and 5.3 g (0.098 mole) of sodium methoxide (Aldrich Chem. Co.) in 150 ml of anhydrous dimethylformamide is added 13.9 g (0.098 mole) of iodomethane dropwise at 23° over a period of 15 minutes and allowed to stir for six hours. After the solution is evaporated under reduced pressure, the residue is taken up with cold water and extracted twice with 150 ml of ethyl acetate. The combined extracts are dried with sodium sulfate and concentrated to a low volume giving 8.7 g of a mixture of both isomers in an approximate ratio 60:40 (A,B), mp 95°–101° C. Passing the filtrate through silica gel gives 3.1 g of additional product (in about the same ratio as above), mp 95°–102° C.

Method B—With Phase-Transfer Catalyst (Adogen 464)

To a vigorously stirred suspension of 5.2 g (0.03 mole) of 1-methyl-2-phenyl-1H-imidazole-4-carboxaldehyde in 100 ml of dichloromethane is added 100 ml of 30% aqueous potassium hydroxide (causing the clear solution). Dimethylsulfate (4.1 g, 0.036 mole) is then added followed by the addition of 1.5 g of Adogen 464 Aldrich Chem. Co.). After two hours at 23°, the two phases are separated and the aqueous phase reextracted with 100 ml of dichloromethane; the combined extracts are dried ($Na_2SO_4$) and evaporated to give 4.6 g of residue which solidifies on standing. The TLC (silica gel; chloroform:methanol:$NH_3$, 90:10:1) shows two spots, $R_f=0.5$ and $R_f=0.6$ corresponding to isomers A and B, respectively.

α-(1-Methyl-2-phenyl-1H-imidazol-4-yl)-4-morpholineacetonitrile and α-(1-Methyl-2-phenyl-1H-imidazol-5-yl)-4-morpholineacetonitrile A solution of 12.1 g (0.186 mole) of potassium cyanide in 12 ml of water is added to a stirred warm (40° C.) solution of 33.7 g (0.181 mole) of a mixture of 1-methyl-2-phenylimidazol-4-carboxaldehyde and of 1-methyl-2-phenylimidazol-5-carboxaldehyde (ca 60:40 ratio), 34.5 g (0.181 mole) of p-toluenesulfonic acid monohydrate, and 31.2 g (0.362 mole of morpholine in 200 ml of dry dioxane and the resulting mixture is refluxed for 90 minutes. After cooling to room temperature, the mixture is poured onto 500 ml of 10% aqueous potassium carbonate solution and extracted twice with 500 ml of dichloromethane. The combined extracts are washed first with saturated aqueous sodium bisulfite solution, then with water, dried over sodium sulfate and evaporated. The cake-like residue is crystallized from ether giving 42.2 g (83% yield) of a mixture of α-(1-methyl-2-phenyl-1H-imidazol-4-yl)-4-morpholineacetonitrile and α-(1-methyl-2-phenyl-1H-imidazol-5-yl)-4-morpholineacetonitrile (about 55:45 ratio), mp 118°–120° C.

Anal. calcd for $C_{16}H_{18}N_4O$: C, 68.06; H, 6.43; N, 19.85. Found: C, 67.83, H, 6.37, N, 19.72.

α-(1-Methyl-2-phenyl-1H-imidazol-4-yl)-4-morpholinebutanenitrile and γ-(1-Methyl-2-phenyl-1H-imidazol-5-yl)-4-morpholinebutanenitrile Acrylonitrile [6.0 g (0.113 mole)] is added dropwise to a solution of 21.0 g (0.0745 mole) of a mixture of α-(1-methyl-2-phenyl-1H-imidazol-4-yl)-4-morpholineacetonitrile and of α-(1-methyl-2-phenyl-1H-imidazol-5-yl)-4-morpholineacetonitrile in 175 ml of dry tetrahydrofuran containing 5 ml of 30% methanolic potassium hydroxide at 23° and is allowed to stir for two hours. The infrared absorption spectrum shows two cyano functions at 2220 and 2228 $cm^{-1}$, respectively, and the pmr spectrum shows absence of the lone proton at δ4.80.

1-Methyl-γ-oxo-2-phenyl-1H-imidazole-4-butanenitrile and 1-Methyl-γ-oxo-2-phenyl-1H-imidazole-5-butanenitrile One half of the above solution is heated with 75 ml of 80% aqueous acetic acid on a steam bath for two hours and subsequently is evaporated in vacuo. The residue is taken up with cold aqueous potassium bicarbonate solution and extracted twice with 500 ml of dichloromethane. The combined organic extracts are washed, dried over sodium sulfate, and evaporated to dryness. Crystallization of the residue from 2-propanol gives 6.1 g (68% yield) of 1-methyl-γ-oxo-2-phenyl-1H-imidazole-4-butanenitrile and of 1-methyl-γ-oxo-2-phenyl-1H-imidazole-5-butanenitrile (approximate ratio 60:40) as white crystals, 98°–100° C.

Anal. calcd for $C_{14}H_{13}N_3O$: C, 70.27; H, 5.48; N, 17.56. Found: C, 70.33; H, 5.58; N, 17.58.

Method B—Direct transformation of the bis-nitrile complex to 1-methyl-γ-oxo-2-phenyl-1H-imidazole-4-butanoic Acid One half of the bis nitrile complex is evaporated and treated with 40 ml of 20% hydrochloric acid at 100° C. for six hours. After the solution is evaporated in vacuo, the residue is taken up with cold 20% sodium hydroxide to pH 10.0, the nonacidic materials are extracted with ether-ethyl acetate, and discarded. The alkaline solution is treated with glacial acetic acid at 0° C. to pH 5.5 causing partial precipitation of the solid. Recrystallization of the latter from ethyl acetate gives 1-methyl-γ-oxo-2-phenyl-1H-imidazole-4-butanoic acid, mp 191°–192° C. The mother liquor and aqueous solution contain a mixture of both isomers.

Anal. calcd for $C_{14}H_{14}N_2O_3$: C, 65.10; H, 5.46; N, 10.85. Found: C, 64.81; H, 5.36; N, 10.72.

4,5-Dihydro-6-(1-methyl-2-phenyl-1H-imidazol-4-yl)-3(2H)-pyridazinone (Isomer A)

A mixture of 1-methyl-γ-oxo-2-phenyl-1H-imidazole-4-butanoic acid and of 1-methyl-γ-oxo-2-phenyl-1H-imidazole-5-butanoic acid (as obtained by method B, ca 60:40 ratio) in 150 ml of ethanol and 25 ml of glacial acetic acid is treated with 12 ml of hydrazine hydrate at 85° C. for six hours and then is allowed to stand overnight at room temperature. The solid is collected, washed with water, then with cold ethanol, and finally with ether giving 4.2 g of pure 4,5-dihydro-6-(1-methyl-2-phenyl-1H-imidazol-4-yl)-3(2H)-pyridazinone as nearly white crystals, mp 271°–272° C., dec.

Anal. calcd for $C_{14}H_{14}N_4O$: C, 66.12; H, 5.55; N, 22.04. Found: C, 66.03; H, 5.59; N, 21.89.

4,5-Dihydro-6-(1-methyl-2-phenyl-1H-imidazol-5-yl)-3(2H)-pyridazinone (Isomer B)

The filtrate from the isomer A is made slightly basic (pH 8.0) with ammonium hydroxide and extracted three times with 150 ml of ethyl acetate. The combined extracts are washed with saturated aqueous sodium chloride, dried over sodium sulfate, and concentrated giving 2.7 g of pure 4,5-dihydro-6-(1-methyl-2-phenyl-1H-imidazol-5-yl)-3(2H)-pyridazinone as white crystals, mp 214°–215° C., dec.

Anal. calcd for $C_{14}H_{14}N_4O$: C, 66.12; H, 5.55; N, 22.04. Found: C, 65.94; H, 5.41; N, 21.99.

EXAMPLE 2

6-(1-Methyl-2-phenyl-1H-imidazol-4-yl)-3(2H)-pyridazinone

A vigorously stirred mixture of 2.2 g of 4,5-dihydro-6-(1-methyl-2-phenyl-1H-imidazol-4-yl)-3(2H)-pyridazinone, Example 1, Isomer A, MnO₂ (Aldrich Chemical, 12 g) and dioxane (175 ml) is heated to 70° C. for 22 hours. The temperature is raised to 100° C. and maintained there for another 25 hours. Additional MnO₂ (8 g) is added and refluxing continued for an additional 20 hours. The mixture is filtered, washed with hot dioxane, and finally with warm tetrahydrofuran. The combined filtrate and washings are concentrated to a small volume to yield 0.9 g of 6-(1-methyl-2-phenyl-1H-imidazol-4-yl)-3(2H)-pyridazinone, as off-white crystals, mp 291°–292° C., dec.

Anal. calcd for $C_{14}H_{12}N_4O$: C, 66.65; H, 4.79; N, 22.21. Found: C, 66.36; H, 5.09; N, 22.48.

4,5-Dihydro-6-(1-methyl-2-phenyl-1H-imidazol-5-yl)-3-(2H)-pyridazinone, Example 1, Isomer B, on similar treatment with MnO₂ in dioxane gave 6-(1-methyl-2-phenyl-1H-imidazol-5-yl)-3(2H)-pyridazinone, mp 288°–290° C. dec.

Anal. calcd for $C_{14}H_{12}N_4O$: C, 66.65; H, 4.79; N, 22.21. Found: C, 66.92, H, 5.09; N, 22.38.

The usefulness of the compounds of the present invention as cardiotonic agents is demonstrated by their effectiveness in standard pharmacological test procedures, for example, in causing a significant increase in the myocardial contractility in the pentobarbital-anethetized dog with low or minimal changes in heart rate and blood pressure. This test procedure is described in the following paragraphs.

Test for In Vivo Myocardial Inotropic Activity in Anesthetized Dog

This screen consists of determining the effects of increasing intravenous doses of compound on myocardial contractility (dP/dt max of left ventricular blood pressure), heart rate, and aortic blood pressure of the pentobarbital-anesthetized dog.

Methods

Adult mongrel dogs of either sex are anesthetized with pentobarbital, 35 mg/kg, IV, and are subsequently maintained under anesthesia with a continuous infusion of pentobarbital, 3.5 mg/kg/hour. The trachea is intubated but the animals are permitted to breathe spontaneously. A cannula is inserted into the femoral vein for administrating test agents. A Millar catheter tip pressure transducer or a fluid filled catheter is inserted into the ascending aorta via the femoral artery for measuring aortic blood pressure. A Millar catheter tip pressure transducer is passed into the left ventricle via the left carotid artery for measuring left ventricular blood pressure. Needle electrodes are placed subcutaneously for recording a lead II electrocardiogram (ECG).

Left ventricular and aortic blood pressures are recorded on a strip chart recorder. Heart rate, using a biotachometer triggered from the R wave of the ECG, and the first derivative of left ventricular blood pressure (dP/dt), obtained with a differentiator amplifier coupled to the corresponding pressure amplifier, are also recorded. A period of at least 30 minutes is utilized to obtain control data prior to administration of test compound.

Depending on solubility, the compounds are dissolved in 0.9% saline solution or in dilute HCl or NaOH (0.1 or 1.0N) and are diluted to volume with normal saline. Ethanol or dimethylacetamide can be used as solvents if adequate dilutions can be made. Appropriate vehicle controls are administered when needed.

Each dose of the test compound is administered in a volume of 0.1 ml/kg over a period of one minute.

When tested by the above-described Anesthetized Dog Procedure, the compounds of the present invention when administered intravenously at a rate of about 0.01 to 0.31 mg/kg/min cause dose related significant increases in cardiac contractility with only low or minimal changes in heart rate and moderate reduction in blood pressure. Thus the compounds of the present invention are also useful as antihypertensive agents.

What is claimed is:

1. A compound of the formula

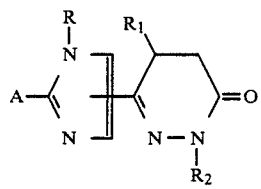

wherein ⋯ is a single or double bond; A is hydrogen, lower alkyl, phenyl, phenyl substituted by lower alkyl, halo or trifluoromethyl, or pyridinyl; R, R₁, and R₂ are independently hydrogen or lower alkyl, and pharmaceutically acceptable acid addition salts thereof.

2. A compound as claimed in claim 1 and of the formula

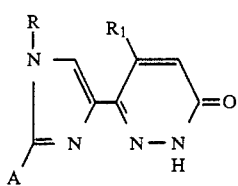

3. A compound as claimed in claim 2, wherein R and R₁ are independently hydrogen or methyl, and A is phenyl.

4. A compound as claimed in claim 1 and of the formula

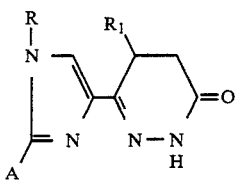

5. A compound as claimed in claim 4, wherein R and R₁ are independently hydrogen or methyl, and A is phenyl.

6. A compound as claimed in claim 4 and being 4,5-dihydro-6-(1-methyl-2-phenyl-1H-imidazol-4-yl)-3(2H)-pyridazinone.

7. A compound as claimed in claim 3 and being 6-(1-methyl-2-phenyl-1H-imidazol-4-yl)-3(2H)-pyridazinone.

8. A pharmaceutical composition for increasing cardiac contractility or lowering blood pressure comprising an effective amount of a compound as claimed in claim 1 with a pharmaceutically acceptable carrier.

9. The method for increasing cardiac contractility in a patient requiring such treatment which comprises administering orally or parenterally to such patient an effective amount of a compound as claimed in claim 1 and a pharmaceutically acceptable carrier.

10. The method of lowering blood pressure in a patient suffering from hypertension which comprises administering orally or parenterally to such patient an effective amount of a compound as claimed in claim 1 and a pharmaceutically acceptable carrier.

* * * * *